(12) United States Patent
Sforazzini

(10) Patent No.: US 10,144,744 B2
(45) Date of Patent: Dec. 4, 2018

(54) COMPOUND FOR USES IN OPTICAL AND ELECTROOPTICAL DEVICES

(71) Applicant: ECOLE POLYTECHNIQUE FEDERALE DE LAUSANNE (EPFL), Lausanne (CH)

(72) Inventor: Giuseppe Sforazzini, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/193,630

(22) Filed: Jun. 27, 2016

(65) Prior Publication Data

US 2017/0369508 A1   Dec. 28, 2017

(51) Int. Cl.
*C07D 498/14* (2006.01)
*C07C 245/08* (2006.01)
(Continued)

(52) U.S. Cl.
CPC .......... *C07D 498/14* (2013.01); *C07C 245/08* (2013.01); *C08G 61/126* (2013.01); *C09K 9/02* (2013.01); *C08G 2261/226* (2013.01); *C08G 2261/228* (2013.01); *C08G 2261/3229* (2013.01); *C08G 2261/364* (2013.01); *C08G 2261/57* (2013.01); *C08G 2261/91* (2013.01); *C08G 2261/92* (2013.01); *C08G 2261/95* (2013.01); *C09K 2211/1007* (2013.01); *C09K 2211/1092* (2013.01); *C09K 2211/1425* (2013.01); *C09K 2211/1458* (2013.01);
(Continued)

(58) Field of Classification Search
CPC ... C07C 245/08; C07C 245/10; C07D 249/24; C07D 251/68; C08J 3/28; C08G 83/00
See application file for complete search history.

(56) References Cited

U.S. PATENT DOCUMENTS 9,085,661 B1 * 7/2015 Tan .................... C08G 73/1007

OTHER PUBLICATIONS

Jiang et al. Polymers move in response to light. Advanced Materials, 2006, vol. 18, pp. 1471-1475. (Year: 2006).*

(Continued)

*Primary Examiner* — Stephen E Rieth
(74) *Attorney, Agent, or Firm* — Sughrue Mion, PLLC

(57) ABSTRACT

A compound having the following formula:

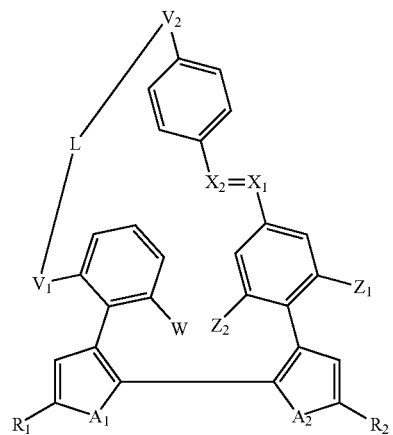

which can also be embedded into a conjugated oligomeric of polymeric backbone, is proposed for optical and electro optical applications.

20 Claims, 2 Drawing Sheets

(51) Int. Cl.
    *C09K 9/02*      (2006.01)
    *H01L 51/42*     (2006.01)
    *H01L 51/05*     (2006.01)
    *H01L 51/50*     (2006.01)
    *C08G 61/12*     (2006.01)
(52) U.S. Cl.
    CPC .......... *H01L 51/0508* (2013.01); *H01L 51/42* (2013.01); *H01L 51/50* (2013.01)

(56) References Cited

OTHER PUBLICATIONS

Kim et al. A supramolecular chiroptical switch using an amorphous azobenzene polymer. Advanced Functional Materials, 2006, vol. 16, pp. 2089-2094. (Year: 2006).*

Jousselme et al. Structural control of the electronic properties of photodynamic azobenzene-derivatized pi-conjugated oligothiophenes. Journal of Physical Chemistry A, 2006, vol. 110, pp. 3488-3494. (Year: 2006).*

* cited by examiner

COMPOUND FOR USES IN OPTICAL AND ELECTROOPTICAL DEVICES

TECHNICAL FIELD

The present invention relates to the field of chemical compounds for optical and electro-optical devices as well as to electronic, optical, and electro-optical devices comprising such chemical compounds. More particularly, it relates to a novel light-responsive molecular architecture that can overcome the current limit of the photochromic dyes as molecular actuators in the field of optoelectronics.

PRIOR ART

Photochromic Dyes: Light-responsive molecules able to undergo a color change upon light stimuli are commonly labeled as 'photochromic'. The change of color is normally the result of a conformational change in the molecular structure. Thus, upon light stimuli photochromic molecules undergo molecular motion to convert into their inherent conformers. Such molecules typically reverse to the initial color either thermally or by subsequent irradiation at a different wavelength. A variety of photochromic molecules have been extensively investigated both in solution and in bulk materials, including azobenzene, diarylethene, spiropyran and chromene derivatives, for applications such as data recording, optical switching, non-linear optical device components, or ophthalmic lenses. However, photochromic molecules have never been successfully employed as an active component in optoelectronics devices One of their main limitations for use in optoelectronic applications can be found in their ability to promptly dissipate the harvested energy through molecular motions for their conformational changes.

Organic Semiconductors: π-Conjugated oligomers and polymers are the typical molecular materials used as active component in optoelectronic devices (solar cells, light emitting diodes, filed effect transistors etc.). Upon optical or electrical excitation they are able to dissipate the absorbed energy in form of optical emission (useful for OLED) or as charge conductivity (useful for solar cells and field effect transistors). Due to these features, conducting oligomers and polymers usually do not possess photochromic behavior.

Photochromic Organic Semiconductors: Attempts to incorporate photochromic molecules as monomer units into an oligomer and polymer backbone have shown that the photochromic reversibility efficiency decreases inversely with the enhancement of the oligomer and polymer π-conjugation. The reduced (or suppressed) photochromic behavior in these molecules is the result of additional dissipating channels, such as emissive channels, that compete with the main thermal energy pathway involved in the conformational changes of the molecular structure, which is typical in pristine photochromic dyes.

Conformation Switching in π-Conjugated Structures: It is well-known that the optical and electronic properties of π-conjugated oligomers and polymers strongly depend on the geometric conformation of their π-system. Thus, varying the region-regularity or tuning the steric interactions of lateral substituents are the most common strategies used to tailor the physical properties of π-conjugated oligomers and polymers. For instance, the strong optical response induced by twisting the π-system of polythiophenes has successfully been applied to ion sensing, see e.g. WO-A-9516681.

SUMMARY OF THE INVENTION

Considering the extensive use of π-conjugated molecules, oligomers and polymers as active materials in optoelectronic devices, and given the possibility to tune their optical and electronic properties by modulating their π-bond geometry at the molecular level, a new design for a light-driven molecular actuator able to tailor the optical and electronic properties of π-conjugated systems is proposed. The latter actuator can be envisaged as a chemical motif that can be potentially incorporated into the backbone of π-conjugated systems, e.g. oligomer and polymer, to reversibly modulate their conjugation extension.

The geometrical arrangement of the π-orbitals in organic semiconductors plays a pivotal role for the optoelectronic properties of the resulting bulk materials. Control over the π-bond geometry, e.g. the planarity, of an extended conjugated system offers the possibility to modulate the effective conjugation length of a π-system, thus, allowing for the tuning of optical and electronic properties. A promising way to reversibly modulate the orientation of the π-orbitals in a conjugated structure is to incorporate photochromic segments onto the 'backbone' of the π-system. Attempts to use photochromic molecules as monomer units in a polymer chain have shown that the photo-reversibility efficiency decreases inversely with the enhancement of the π-conjugation. In the present invention a novel molecular architecture is proposed, referred to as a 'photochromic torsional switch' (PTS), which can overcome the limits of today's photochromic dyes towards their incorporation into extended π-systems. The aforementioned molecular structure comprises a polymerizable conjugated twistable backbone segment, for example a bithiophene unit, able to mechanically change its π-system planarity in response to the molecular motion of a preferably laterally and/or orthogonally (with respect to the conjugated system of the main chain) attached light-responsive unit, e.g. azobenzene. In the dark and upon exposure of light with a specific wavelength, e.g. 254 nm light, the azobenzene moiety assumes its extended trans conformation, thus, forcing the bithiophene backbone to twist out of coplanarity. By contrast, exposure to light with another wavelength, e.g. 350 nm light, results in isomerization of the azobenzene unit to the cis conformation, which allows the bithiophene fragment to assume a planar, π-conjugated conformation. The PTS architectures, proposed in this work, represent a new generation of light-mediated actuators (or multicomponent photochromic dyes-based derivatives) that can allow (for the first time) preparation of 'conjugated light-responsive polymers' (or other light-responsive structures with an extended π-system), which can be used as active smart material in optoelectronic devices.

So a novel molecular architecture is proposed, made of tree different parts: a light responsive switch, a polymerizable π-conjugated fragment, e.g. a dimer, and a linker. The PTS actuator preferably consists of an azobenzene-switch connected to a backbone, preferably bithiophene unit, by both direct and aliphatic linker-assisted bonding. Two side functionalities, preferably methyl units, in the meta position of the azobenzene can be used to guarantee its orientation in an orthogonal arrangement to the bithiophene fragment, to suppress significantly the potentially detrimental reduction of photo-switchability of the azobenzene due to the communication between the π-orbitals of the two constituents. Preferably a ten-carbon alkene chain connected with an alkoxy benzene unit transfers mechanically the motion of the azobenzene to the bithiophene backbone.

This PTS unit can then be incorporated as a repeating unit into π-conjugated oligomers and polymers, so that when these PTS-containing structures are excited at a specific wavelength, e.g. 254 nm, or not exposed to light, the azobenzene moiety, if used as the light-responsive switch, assumes its extended trans conformation, which forces the bithiophene backbone, if used as the backbone in the PTS unit, to twist out of coplanarity. By contrast, the exposure to light with a different wavelength, e.g. 350 nm, will result in isomerization of the azobenzene unit to the cis conformation, which allows the bithiophene fragment to assume a planar, π-conjugated conformation. The conversion from one azobenzene photoisomer to the other one, hence, 'mechanically' regulates the geometry of the π-conjugated system, transmitted by the linker between the azobenzene and the bithiophene. The twisting of the π-conjugated oligomers and polymers backbone will shift its absorption below 400 nm and, thus, render the polymer poorly conductive. On the other hand, the planar conformation of the oligomers and polymers on the cis isomerization of the azobenzene will shift the absorption above 400 nm and make the oligomers and polymers colorful and highly conductive.

More generally speaking, the present invention relates to a compound having the following formula:

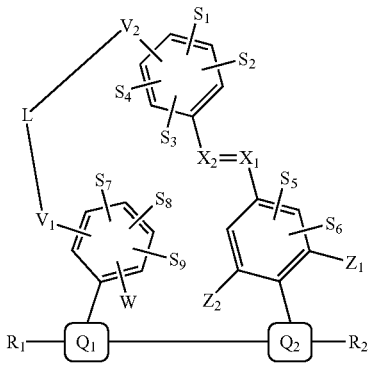

wherein $Q_1$, $Q_2$ are one or a mixture of π-conjugated aromatic cores;

$R_1$ and $R_2$ are selected, independently from each other, from the following group: H, halogen, methyl, $Sn(R_{R,1})_3$, $B(OH)_2$, $OR_{R,2}$, $NR_{R,3}R_{R,4}$, $NO_2$, $COOR_{R,5}$, $COR_{R,6}$, $S_{R,7}$, —CN, —$CCR_{R,8}$, —$SO_3H$, —C=$C(CN)_2$, —C=C$(CN)(COOR_{R,9})$, —$C(CN)$=$C(CN)_2$, substituted and unsubstituted ferrocene and derivatives thereof, substituted and unsubstituted pyridine and derivatives thereof, including pyridinium groups, pentafluorophenol, substituted and unsubstituted fullerene and derivatives thereof;

with the residues $R_{R,1}$, —$R_{R,9}$ selected, independently from each other, from the group consisting of: methyl, ethyl, propyl, isopropyl, phenyl, benzyl, and primary, secondary, and tertiary amines;

$V_1$ and $V_2$ are selected, independently from each other, from the following group: $CH_2$, S, O, NH, COO, CO, $CONR_{V,1}$, $NR_{V,2}CO$, with the residues $R_{V,1}$-$R_{V,2}$ selected, independently from each other, from the group consisting of H, methyl, ethyl, propyl, isopropyl, phenyl or benzyl;

$X_1$ and $X_2$ are selected, independently from each other, from the following group: N, CH;

$Z_1$ and $Z_2$ are selected, independently from each other, from the following group: halogen, methyl, ethyl, propyl, isopropyl, phenyl and benzyl, $SR_{Z,1}$, $OR_{Z,2}$, $COOR_{Z,3}$, $NR_{Z,4}R_{Z,5}$ $NO_2$, —CN, —$SO_3H$, with the residues $R_{Z,1}$-$R_{Z,5}$ selected, independently from each other, from the group consisting of H, methyl, ethyl, propyl, isopropyl, benzyl, primary, secondary, and tertiary amines;

L is a hydrocarbon chain with 5-15 carbon atoms in which up to 3 hydrocarbon moieties (—$CH_2$—) can be replaced by one of the following moieties: O, $NR_{L,1}$, S, and/or in which there can be up to 3 double or triple bonds, in which pairs of the type —$CH_2$—$CH_2$— are replaced by —$R_{L,2}$C=$CR_{L,3}$—, or —N=$CR_{L,4}$—, with the residues $R_{L,1}$-$R_{L,4}$ selected, independently from each other, from the group consisting of H, methyl, ethyl, propyl, isopropyl or benzyl;

W is selected from the group consisting of: H, halogen, $SR_{W,1}$, methyl, ethyl, $OR_{W,2}$, $COOR_{W,3}$, with the residues $R_{W,1}$-$R_{W,3}$ selected, independently from each other, from the group consisting of H, methyl, ethyl, propyl, isopropyl, phenyl or benzyl.

$S_1$—$S_9$ are selected, independently from each other, from the group consisting of: H, halogen, methyl, ethyl, phenyl, benzyl, $OR_{S,1}$, $SR_{S,2}$, $COOR_{S,3}$, $COR_{S,4}$, $NR_{S,5}R_{S,6}$, $CONR_{S,7}$, $NR_{S,8}CO$, $NO_2$, $SO_3H$, with the proviso that pairs of $S_1$—$S_4$, $S_5$ and $S_6$, $S_7$—$S_9$ can be given by bridging conjugated structural elements selected from the group consisting of:

ortho $(CH)_2$-benzene (thus forming a substituted or unsubstituted anthracene core)

—$(CR_{S,9})(CR_{S,10})(CR_{S,11})$—, —$(CR_{S,12})(CR_{S,13})(CR_{S,14})(CR_{S,15})$—, —$(CR_{S,16})(CR_{S,17})(CR_{S,18})(CR_{S,19})(CR_{S,20})$—, in which $CR_{S,N}$ moieties can be replaced by N, NH, O, and/or S, with the residues $R_{S,1}$-$R_{S,20}$ selected from the group consisting of H, methyl, ethyl, propyl, isopropyl, phenyl or benzyl.

In such a compound, according to a preferred embodiment, at least one of $Q_1$ and $Q_2$, preferably both, is given by one of the following structural moieties:

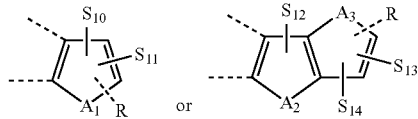

wherein $A_1$, $A_2$, and $A_3$ are selected, independently from each other, from the following group: S, O, NH, $NR_{A,1}$, BH, $BR_{A,1}$, $PR_{A,1}$, $PR_{A,1}R_{A,2}$, Se, CH=CH, CH=N, CH=$PR_{A,11}$, $CH=PR_{A,11}R_{A,2}$, $CH_2$, $C=O$, $C=CH_2$, $C=CR_{A,1}R_{A,2}$, with the residues $R_{A,1}$ and $R_{A,2}$ selected, independently from each other, from the group consisting of H, methyl, ethyl, propyl or benzyl;

$S_{10}$—$S_{14}$ are selected, independently from each other, from the group consisting of: H, halogen, methyl, ethyl, phenyl, benzyl, $OR_{S,21}$, $SR_{S,22}$, $COOR_{S,23}$, $COR_{S,24}$, $NR_{S,25}R_{S,26}$, $CONR_{S,27}$, $NR_{S,28}CO$, $NO_2$, $SO_3H$, with the proviso that pairs of $S_{10}$—$S_{11}$, $S_{13}$ and $S_{14}$ can be given by bridging conjugated structural elements selected from the group consisting of:

ortho $(CH)_2$-benzene (thus forming a substituted or unsubstituted anthracene core)

—$(CR_{S,29})(CR_{S,30})(CR_{S,31})$—, —$(CR_{S,32})(CR_{S,33})(CR_{S,34})(CR_{S,35})$—, —$(CR_{S,36})(CR_{S,37})(CR_{S,38})(CR_{S,39})(CR_{S,40})$—, in which $CR_{S,N}$ moieties can be replaced by N, NH, O, and/or S, with the residues $R_{S,21}$-$R_{S,40}$ selected from the group consisting of H, methyl, ethyl, propyl, isopropyl, phenyl or benzyl.

According to a further preferred embodiment, the compound has the following structure:

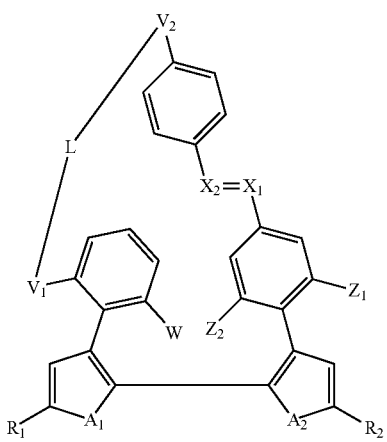

wherein L is defined above as the hydrocarbon chain, and in which the residues $Q_1$, $Q_2$ are 5 or 6 membered π-conjugated aromatic cores, in which $A_1$ and $A_2$ are selected, independently from each other, from the following group: S, O, NH, $NR_{A,1}$, BH, $BR_{A,1}$, $PR_{A,1}$, $PR_{A,1}R_{A,2}$, Se, $CH=CH$, $CH=N$, $CH=PR_{A,1}$, $CH=PR_{A,1}R_{A,2}$, $CH_2$, $C=O$, $C=CH_2$, $C=CR_{A,1}R_{A,2}$, with the residues $R_{A,1}$ and $R_{A,2}$ selected, independently from each other, from the group consisting of H, methyl, ethyl, propyl or benzyl.

In other words the backbone element, to which the light-driven switch is connected, is a π-conjugated system with two cycloaromatic building blocks. These building blocks can be 6 membered or 5 membered rings, as well as a single ring or two fused rings and they are connected by one bond providing a rotational degree of freedom, such that if the two rings are arranged essentially in one plane, the conjugation extends over both rings, while if the two rings are arranged essentially in staggered position around this bond, the conjugation is reduced or disrupted. The light-driven molecular switch is orthogonally connected to this backbone structure to allow for changing the rotational position around this bond.

In a three-dimensional representation, when Q is a single aromatic ring, $S_1$—$S_9$, $S_{11}$ are H, L is a linear alkyl chain, W and $V_1$ are in meta and $V_2$ in para, the structure can be given as follows, wherein a different notation however is used for the variable groups:

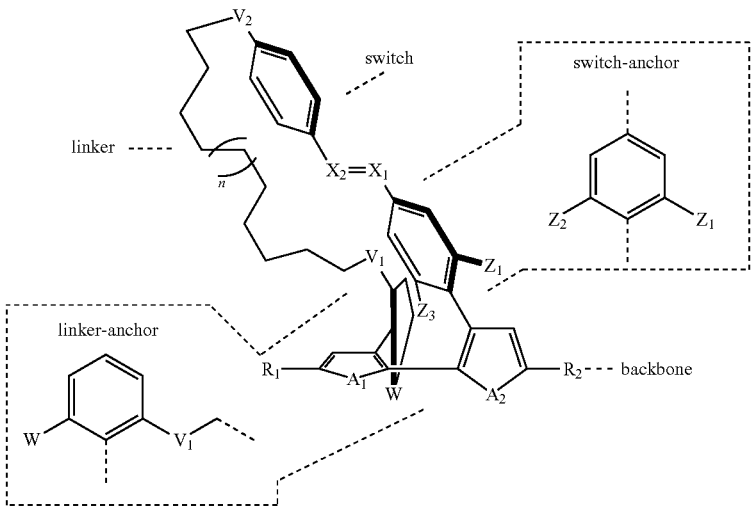

The linker can have different numbers of atoms, and compositions including, C, O, N, S, double- and triple-bonds.

The functioning of the PTS switch can be illustrated as follows, wherein a different notation however is used for the variable groups:

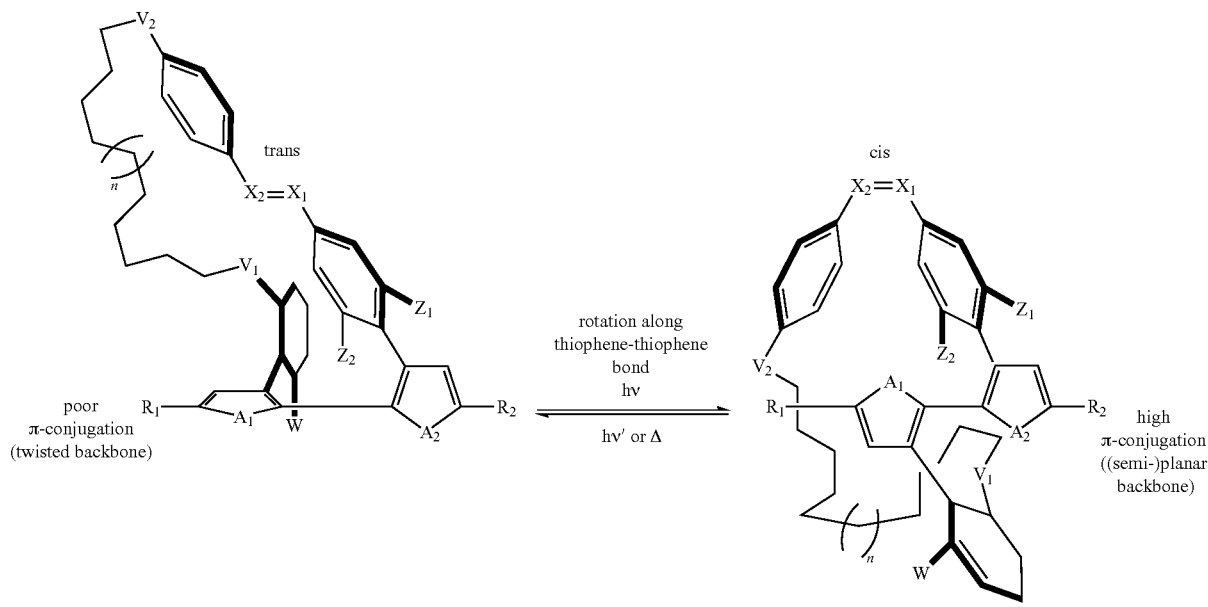

A possible synthetic pathway to generate structures of this type can be summarized as follows for a particular choice of the building blocks:

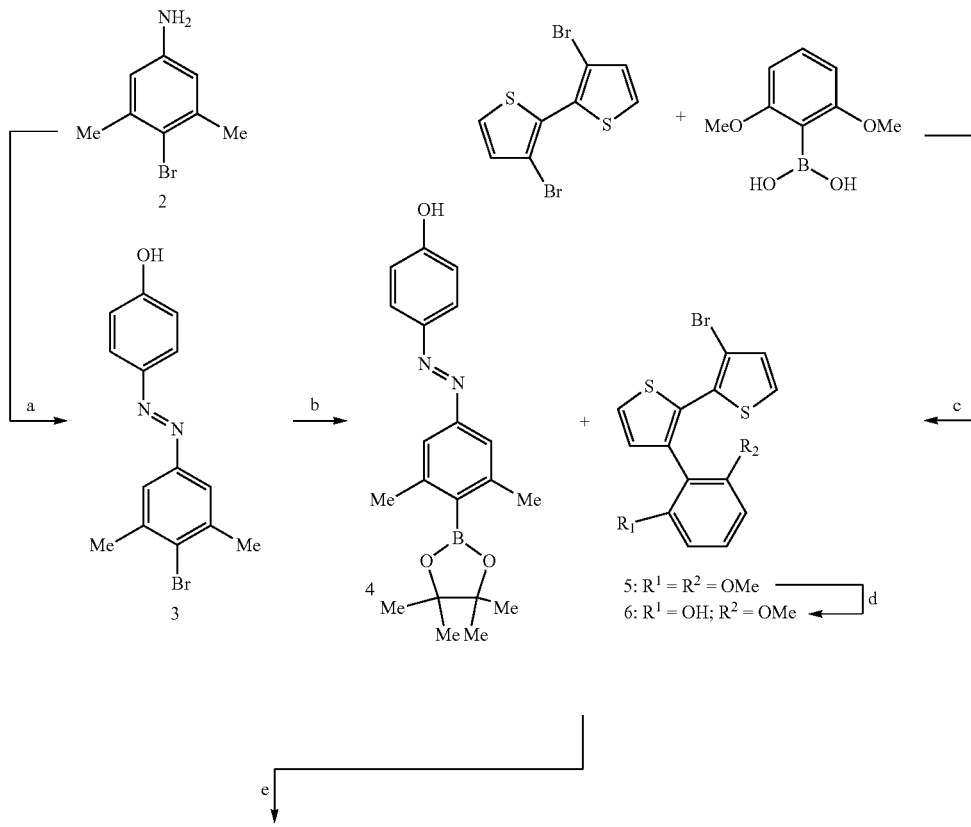

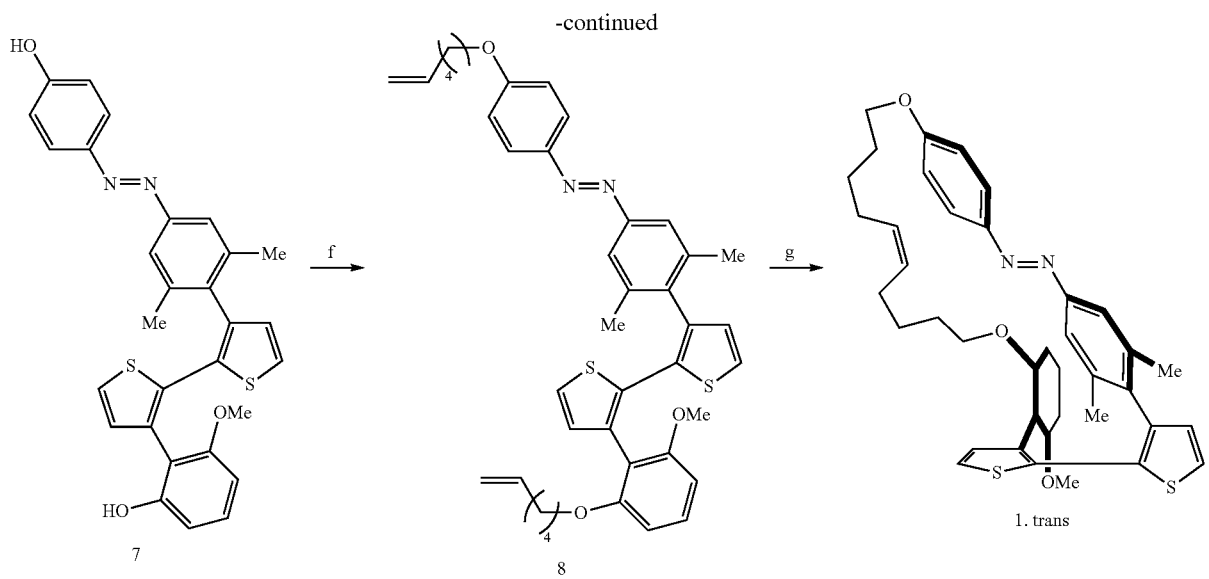

Also, this building block can be incorporated into a larger conjugated system, so the present invention also relates to a compound having the following formula:

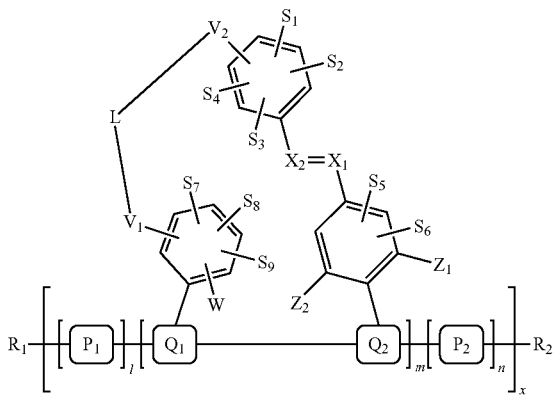

wherein
$Q_1$, $Q_2$ are one or a mixture of π-conjugated aromatic cores;
$R_1$ and $R_2$ are selected, independently from each other, from the following group: H, halogen, methyl, $Sn(R_{R,1})_3$, $B(OH)_2$, $OR_{R,2}$, $NR_{R,3}R_{R,4}$, $NO_2$, $COOR_{R,5}$, $COR_{R,6}$, $S_{R,7}$, —CN, —$CCR_{R,8}$, —$SO_3H$, —C=C(CN)$_2$, —C=C(CN)(COOR$_{R,9}$), —C(CN)=C(CN)$_2$, substituted and unsubstituted ferrocene and derivatives thereof, substituted and unsubstituted pyridine and derivatives thereof, including pyridinium groups, pentafluorophenol, substituted and unsubstituted fullerene and derivatives thereof; with the residues $R_{R,1}$, —$R_{R,9}$ selected, independently from each other, from the group consisting of: methyl, ethyl, propyl, isopropyl, phenyl, benzyl, and primary, secondary, and tertiary amines;
$V_1$ and $V_2$ are selected, independently from each other, from the following group: $CH_2$, S, O, NH, COO, CO, $CONR_{V,1}$, $NR_{V,2}CO$, with the residues $R_{V,1}$-$R_{V,2}$ selected, independently from each other, from the group consisting of H, methyl, ethyl, propyl, isopropyl, phenyl or benzyl;
$X_1$ and $X_2$ are selected, independently from each other, from the following group: N, CH;
$Z_1$ and $Z_2$ are selected, independently from each other, from the following group: halogen, methyl, ethyl, propyl, isopropyl, phenyl and benzyl, $SR_{Z,1}$, $OR_{Z,2}$, $COOR_{Z,3}$, $NR_{Z,4}R_{Z,5}$, $NO_2$, —CN, —$SO_3H$, with the residues $R_{Z,1}$-$R_{Z,5}$ selected, independently from each other, from the group consisting of H, methyl, ethyl, propyl, isopropyl, benzyl, primary, secondary, and tertiary amines;
L is a hydrocarbon chain with 5-15 carbon atoms in which up to 3 hydrocarbon moieties (—$CH_2$—) can be replaced by one of the following moieties: O, $NR_{L,1}$, S, and/or in which there can be up to 3 double or triple bonds, in which pairs of the type —$CH_2$—$CH_2$— are replaced by —$R_{L,2}$C=$CR_{L,3}$—, or —N=$CR_{L,4}$—, with the residues $R_{L,1}$-$R_{L,4}$ selected, independently from each other, from the group consisting of H, methyl, ethyl, propyl, isopropyl or benzyl;
W is selected from the group consisting of: H, halogen, $SR_{W,1}$, methyl, ethyl, $OR_{W,2}$, $COOR_{W,3}$, with the residues $R_{W,1}$-$R_{W,3}$ selected, independently from each other, from the group consisting of H, methyl, ethyl, propyl, isopropyl, phenyl or benzyl.
$S_1$-$S_9$ are selected, independently from each other, from the group consisting of: H, halogen, methyl, ethyl, phenyl, benzyl, $OR_{S,1}$, $SR_{S,2}$, $COOR_{S,3}$, $COR_{S,4}$, $NR_{S,5}R_{S,6}$, $CONR_{S,7}$, $NR_{S,8}CO$, $NO_2$, $SO_3H$,
with the proviso that pairs of $S_1$-$S_4$, $S_5$ and $S_6$, $S_7$-$S_9$ can be given by bridging conjugated structural elements selected from the group consisting of:
ortho (CH)$_2$-benzene (thus forming a substituted or unsubstituted anthracene core),
—(CR$_{S,9}$)(CR$_{S,10}$)(CR$_{S,11}$)—, —(CR$_{S,12}$)(CR$_{S,13}$)(CR$_{S,14}$)(CR$_{S,15}$)—, —(CR$_{S,16}$)(CR$_{S,17}$)(CR$_{S,18}$)qj(CR$_{S,19}$)(CR$_{S,20}$)—, in which CR$_{S,N}$ moieties can be replaced by N, NH, O, and/or S,
with the residues $R_{S,1}$-$R_{S,20}$ selected from the group consisting of H, methyl, ethyl, propyl, isopropyl, phenyl or benzyl
$P_1$, $P_2$ are one or a mixture of π-conjugated aromatic cores
l is selected to be an integer in the range of 0-10
m is selected to be an integer in the range of 1-10
n is selected to be an integer in the range of 0-10
x is selected to be an integer in the range of 1-10,000
with the proviso that l+n is at least 1.

As for the residues $P_1$ and $P_2$, these can independently, according to a preferred embodiment, preferably both, be selected from the following structural building blocks, which can be substituted or unsubstituted, in case of substitution preferably by halogen, methyl, ethyl, proper, isopropanol, benzyl, phenyl:

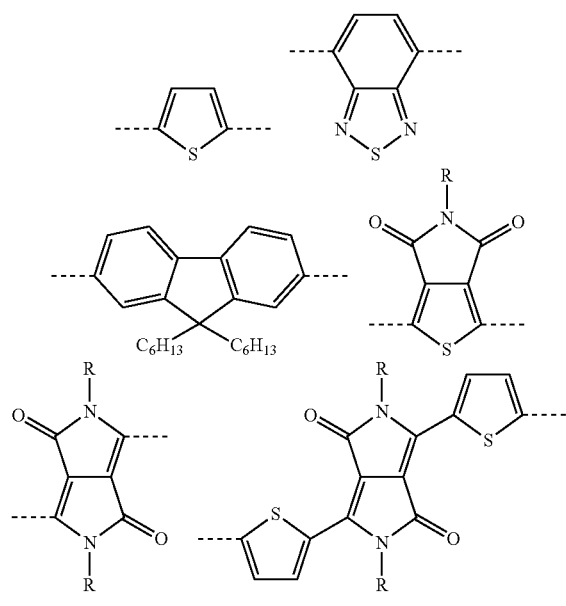

According to a preferred embodiment, the compound has the following structure:

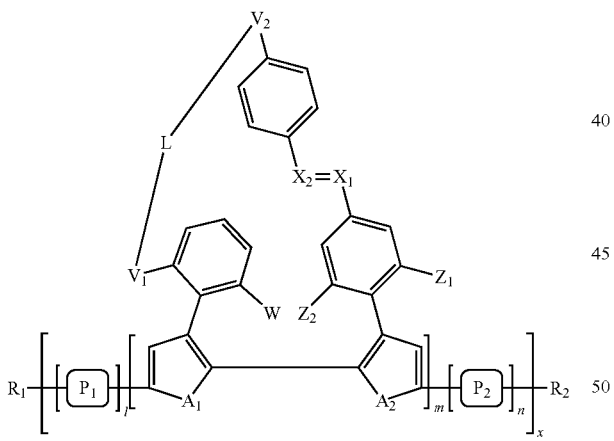

wherein L is defined above as the hydrocarbon chain, and in which the residues $Q_1$, $Q_2$ are 5 or 6 membered π-conjugated aromatic cores, in which $A_1$ and $A_2$ are selected, independently from each other, from the following group: S, O, NH, $NR_{A,1}$, BH, $BR_{A,1}$, $PR_{A,1}$, $PR_{A,1}R_{A,2}$, Se, CH=CH, CH=N, CH=$PR_{A,1}$, CH=$PR_{A,1}R_{A,2}$, $CH_2$, C=O, $C=CR_2$, $C=CR_{A,1}R_{A,2}$, with the residues $R_{A,1}$ and $R_{A,2}$ selected, independently from each other, from the group consisting of H, methyl, ethyl, propyl or benzyl.

Furthermore in this structure there is provided an extension of the conjugated backbone which is provided by the unit $P_1$ and $P_2$, which can be given by one single kind of π-conjugated aromatic cores, e.g. thiophene, but it can also be composed of several different monomer building blocks providing for the corresponding conjugation, so a mixture of thiophene and 2,1,3-benzothiadiazole just to give an example. The integers l, m and n, giving the number of these building blocks $P_1$ and $P_2$, is selected to be an integer in the range of 1-10, however l can also assume a value of 0, and x, the number of the repeating units, is selected to be an integer in the range of 1-10,000.

So the PTS unit can be incorporated as sole or repeating unit in π-conjugated oligomers and polymers, again when Q is a single aromatic ring, $S_1$-$S_9$, $S_{11}$ are H, L, is a linear alkyl chain, W and $V_1$ are in meta and $V_2$ in para, the three-dimensional structure can be illustrated as follows:

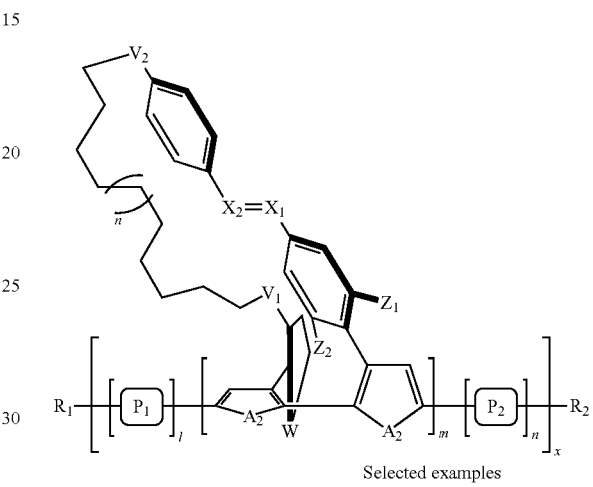

Selected examples

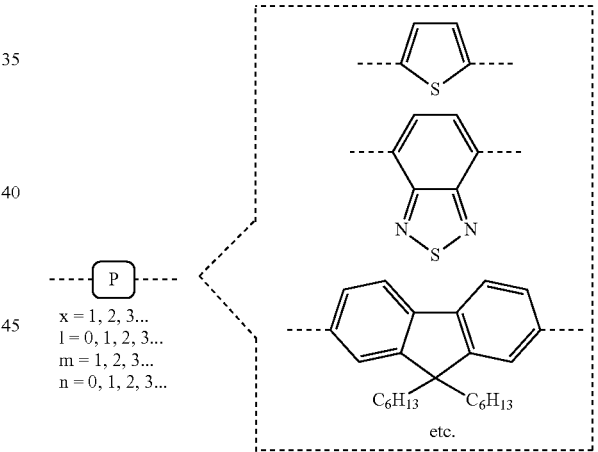

x = 1, 2, 3...
l = 0, 1, 2, 3...
m = 1, 2, 3...
n = 0, 1, 2, 3...

The backbone $P_1$ and $P_2$ building block in such π-conjugated oligomers and polymers according to a first preferred embodiment is selected from the group consisting of at least one of: 2,1,3-benzothiadiazole, azole, diazole including imidazole and pyrazole, triazole, tetrazole, thiophene, pyrrole, furan, selenophene, vinylene, selenazole, thiazole, thiadiazole, oxazole, oxadiazole, pyridine, diazine including pyrimidine, triazine, tetrazine, selenazine, thiazine, azepine, diazepine, phenyl based cores, biphenyl based cores, arylamine derivatives including triphenylamine, tetraphenylbenzidine, and carbazole, pyrrole-based macrocycles including porphyrin and phthalocyanine, boron derivatives including triphenylborane, divinylphenyl alkyl and difluoroboradiaza indacene, ethylenedioxythiophene, phosphorus derivatives including triphenylphosphine and triphenylphosphine oxide, perylene derivatives including perylene tetracarboxylic dianhydride, N,N dialkyl perylene dicarboximide, N,N dibenzyl perylene dicarboximide, naphthalene derivatives including naphthalene tetracarboxylic dianhydride, N,N dialkyl naphthalene dicarboximide, N,N dibenzyl naphthalene dicarboximide, polycyclic aromatic hydrocarbons including anthracene, tetrazene, pentacene and pyrene, thienothiophene and its derivatives, benzodithiophene and its derivatives, tetrathiafulvalene and its derivatives. Preferably, at least one of $P_1$ and $P_2$ is selected to be thiophene or a bridged π-conjugated biphenyl.

Further preferably $Q_1$-$Q_2$ are each selected to be thiophene, so also the backbone portion to which the PTS actuator is connected and which is controlled by the light-driven switch is based on thiophene building blocks. These thiophene building blocks may carry certain substitutions, e.g halogen substitutions, methyl groups.

When talking about halogen in the present invention, this refers to chlorine, bromine, iodine, and fluorine, preference being given to chlorine and bromine and iodine.

According to yet another preferred embodiment, $X_1$ and $X_2$ are each selected to be N, so the light responsive switch is selected to be an azobenzene moiety.

$V_1$ and $V_2$ are preferably placed in meta and para respectively with respect to the bridging structural chain between $Q_1$ and $Q_2$, and are selected to be O.

$Z_1$ and $Z_2$ are further preferably each selected to be methyl.

$S_1$-$S_9$, $S_{11}$ more preferably $S_1$-$S_{13}$ are preferably each selected to be H.

W is preferably placed in meta and can be selected from the group consisting of methyl and methoxy, with particular preference being given to methoxy providing optimum steric locking effects.

Preferably l is 1, or n is 1 or m is 1, or all are selected to be 1.

L, the linker element, according to a preferred embodiment is selected to be a hydrocarbon chain with 8-12 carbon atoms, in which up to 2 hydrocarbon moieties can be replaced by one of the following moieties: O, $NR_{L,1}$, S, and in which there can be up to 2 carbon-carbon double or triple bonds, with the residue $R_{L,1}$ selected from the group consisting of H, methyl, ethyl, propyl or benzyl.

L can also be selected to be a $(CH_2)$ chain with 8-12 carbon atoms, in which two of the $(CH_2)$ moieties are replaced by $(CR_{L,1})$ to form a double bond, with the residues $R_{L,1}$ independently from each other, from the group consisting of H, methyl, ethyl, propyl or benzyl.

L can furthermore be selected to be a $(CH_2)$ chain with 10 carbon atoms, and two of the $(CH_2)$ moieties are replaced by $(CR_{L,1})$ to form a double bond, preferably at position 5.

The integer x is preferably selected to be in the range of 1-1,000.

Furthermore the present invention relates to an optical, electronic or electrooptics device comprising a compound as defined above. Such a device may for example comprise a substrate and at least one layer on said substrate, said layer including at least one compound as described above.

The device can for example be a photochromic photovoltaic device, a multicolor organic light emitting diodes device, or a photo tunable organic field effect transistor.

Furthermore the present invention relates to a method of using a compound as described above for the making of an optical, electronic or electrooptics device.

Also it relates to a method for making an optical, electronic or electrooptics device using a compound as described above.

In summary, the proposed invention comprises the following elements:

A novel photochromic molecular architecture, named as photochromic torsional switch (PTS) that can reversibly change the π-conjugation extension of molecules, oligomers, polymers and other extended π-systems.

The change of the π-conjugation extension can be used to tune optical and electronic properties of the π-conjugated molecules, oligomers, polymers and other extended π-systems The change π-conjugation extension is induced by the twisting of the π-orbital as response to the molecular motion of a light-driven switch.

The twisting of the π-orbitals takes place on the backbone of the PTS unit.

The PTS unit comprises or consists of a photoswitch, a linker and a polymerizable conjugated dimer.

The photoswitch is connected with the two units of the backbone-conjugated dimer.

The photoswitch is directly connected to one unit of the dimer and connected with a linker to the other units of the dimer.

The direct bonding of the photo-switch unit, according to a preferred embodiment, with the thiophene allows for the transfer of the motion from the photo-switchable azobenzene to the thiophene adjacent to that bearing the photo-switch.

The two methyl units, according to a preferred embodiment, in the meta positions of the azobenzene break the π-conjugation between the bithiophene and the azobenzene, thus making the photochromicity of the azobenzene independent to the enhancement of the π-conjugation on the bithiophene when it is oligo- or polymerized.

The rotational motion is directed only on the conjugated backbone dimer bond with rotational degree of freedom, according to a preferred embodiment the thiophene-thiophene bond of the PTS unit.

The α-position and β-position of the bithiophene are, according to a preferred embodiment, available for the integration of the PTS unit into π-conjugated systems.

The dihedral angle between the two thiophenes, according to a preferred embodiment, in the PTS units can be tailored by modifying the length of the linker, as well as its anchoring sites.

The thermal relaxation of the cis-planar PTS isomer can be tuned by functionalization of the switch unit, preferably the azobenzene, as well as modifying the linker and controlling the intra molecular interactions of the group of functionalities integrated in α-position and β-position to the bithiophene, according to a preferred embodiment.

The resulting 'light-responsive π-conjugated oligomers and/or polymers' can be incorporated as active part in devices such as:

Photochromic-photovoltaic windows: The PTS-based materials can be tweaked to give a smart material that can be colorless and highly transparent in 'low light' conditions, so as to allow for their use in windows (Note: This scenario is possible if the azobenzene in its trans form induces a torsion along conjugated polymer such that it shifts the absorption spectrum of the polymer in the UV region). However, these smart materials become both more absorbing and conducting upon sunlight exposure, exhibiting absorption over the entire spectral range and, hence, giving rise to an acceptably efficient photovoltaic device. (Note: The sunlight promotes the cis isomerization of the azobenzene resulting in the planarization of the polymer that shifts its absorption spectrum in the visible spectral range, thus rendering the photoconductive and colorful). Like existing photochromic windows, the auto-shading of the windows in sun light would, at the same time, make for desirable in-door environment, reduce the energy demand from the cooling system, and simultaneously be used for energy production.

Multicolor-organic light emitting diode (OLED): The PTS-based materials can be tweaked to give a smart material that can reversibly change the π-conjugation length along the conjugated backbone of the constituents, as response to two or more specific light wavelengths. (Note: This scenario is possible if the azobenzene in its trans form induces a modest torsion along conjugated polymer that does not disrupt completely the conjugation). The different level of conjugation will result in different emissive spectra, allowing for the dynamic tuning of the OLED light.

Phototunable organic field effect transistor (OFET): The PTS-based materials can be tweaked to give a smart material that can reversibly change the π-conjugation length along the conjugated backbone of the constituents, as response to two or more specific light wavelengths. The different level of conjugation will result in different conductivity in the OFET.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
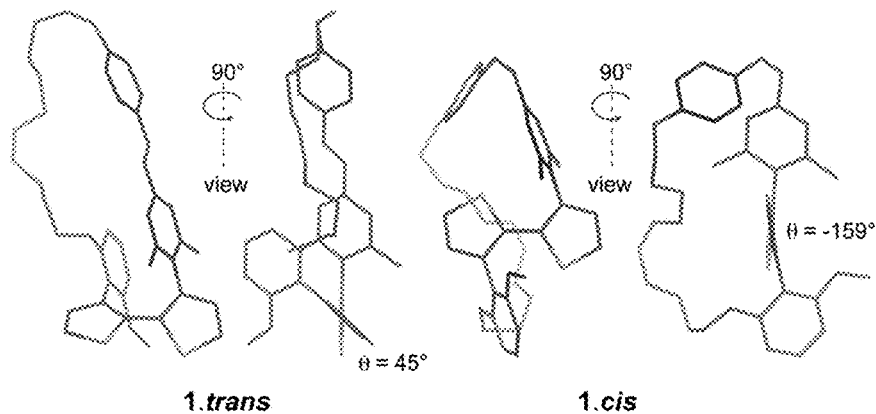
FIG. 1 shows optimized geometries of 1.trans (left) and 1.cis (right) identified from Molecular Mechanics computation.

A molecular architecture is presented that can reversibly change the geometric conformation of its π-system backbone via irradiation with two different wavelengths. The proposed 'molecular actuator' consists of a photoswitchable azobenzene laterally connected to a π-conjugated bithiophene by both direct and aliphatic linker-assisted bonding.

Upon exposure to 350 nm light, the trans azobenzene moiety isomerizes to its cis form, causing the bithiophene to assume a semiplanar anti conformation (high π-conjugation). Exposure to 254 nm light promotes the isomerization of the azobenzene unit back to its initial extended trans conformation, thus forcing the bithiophene fragment to twist out of coplanarity (poor π-conjugation). The molecular conformation of the bithiophene was characterized using steady-state UV-Vis and nuclear magnetic resonance spectroscopy, as well as molecular modeling. The proposed molecular design could be envisaged as a π-conjugation modulator, which has potential to be incorporated into extended linear π-system, i.e. via the terminal α-thiophene positions, and used to modulate their optical and electronic properties.

The ability to control mechanical motion at the molecular level is pivotal for development of novel responsive materials able to translate the functionality of molecules into work. In the last 20 years, a large variety of 'molecular actuators' able to convert thermal, chemical, and photochemical energy into operating motion have been successfully employed to perform tasks at the meso- and macroscopic levels. The restrained mechanistic action of these molecular actuators is commonly correlated with thoughtful design of their dynamic molecular structure. In order to provide different functions, various molecular architectures have been proposed, e.g. shuttles, rotors, scissors, cars, chemical valves, and artificial molecular-based muscles. A number of these molecular actuators have also been successfully engineered to undergo controlled molecular motion and to undertake work on their environment, e.g. cargo lifting, transporting and rotating systems. Despite the large variety of synthetic responsive architectures reported in literature, examples of design conceived to exploit the molecular motion as a means to tune the conjugation length of linear π-systems remain scarce. Molecular actuators designed for the dynamic tuning of π-conjugated molecules are usually limited by the possibility to switch the orientation of their constituents between only two thermodynamically stable semiplanar conformations, syn and anti. The restricted modus operandi of these actuators does not make it possible to obtain highly twisted π-orbital geometries, which if achieved would allow for the full exploitation of the physical properties of π-conjugated systems. The ability to modulate the π-bond geometry of an extended conjugated system offers the possibility to tailor the effective conjugation length of the π-system, thus, allowing for the tuning of its optical and electronic properties.

The dynamic modulation of optoelectronic properties is particularly desirable for the development of novel smart materials that can be used as active components in optoelectronic devices such as organic light emitting diodes (OLEDs), solar cells, field effect transistors (OFETs), etc.

In this line a novel molecular design is proposed here, referred to as a 'Photochromic Torsional Switch' (PTS), able to mechanically change planarity of its π-conjugated backbone, in response to light. PTS actuators are a chemical motif that can be incorporated into the backbone of linear π-systems to reversibly modulate their conjugation length. The design of PTS 1 is illustrated as follows:

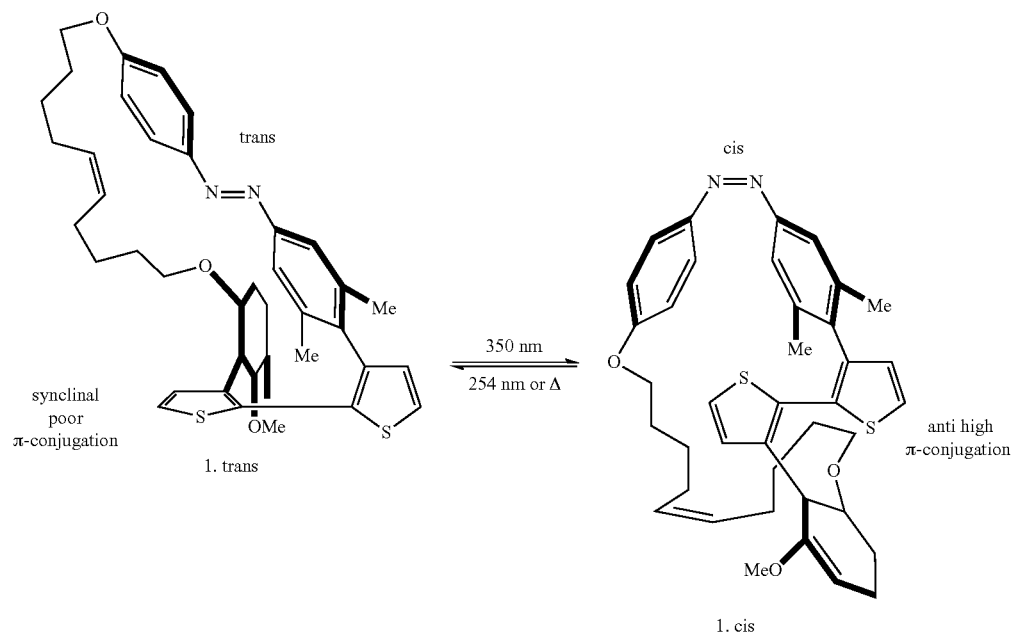

The PTS actuator according to the specifically worked example consists of an azobenzene-switch laterally connected to a bithiophene unit by both direct and aliphatic linker-assisted bonding. Two methyl units in the meta position of the azobenzene guarantees its orientation in an orthogonal arrangement to the bithiophene fragment, thus suppressing significantly the communication between the π-orbitals of the two constituents.

A ten-carbon alkene chain connected with an alkoxy benzene unit transfers mechanically the motion of the azobenzene to the bithiophene backbone. The described PTS actuator 1 was synthetized as the pure trans conformer by intra-molecular cross metathesis of the two terminal alkenes of its open precursor.

The geometrical conformations of both 1.trans and 1.cis, were identified by Molecular Mechanics computations. The lowest-lying structures revealed that when the azobenzene is in its extended trans conformation (1.trans), the bithiophene unit is forced to twist out of coplanarity with a dihedral angle (θ) of 45° (see FIG. 1).

Contrarily, when the azobenzene assumes its cis form (1.cis) the bithiophene assumes a more planar and π-conjugated conformation with θ=−159°. The later dihedral angle is in good agreement with the literature values reported for unsubstituted bithiophenes in their anti-conformation (θ=148°-152°).

On the other hand, the bithiophene configuration in 1.trans has a dihedral angle that significantly differs from the values commonly observed for both anti and syn conformers (θ=35-37°). The synclinal arrangement assumed by the thiophenes in 1.trans is the result of a suppressed rotation along the thiophene-thiophene bond derived by the stretching of the aryloxy alkene linker, which mechanically arrests the bithiophene in a conformation that would be energetically unfavorable for the corresponding unmodified counterparts. In order to probe any structural variations of the bithiophenes, following azobenzene isomerization, we used UV-Vis and nuclear magnetic resonance spectroscopy, and electronic structure computations.

Figure 2:
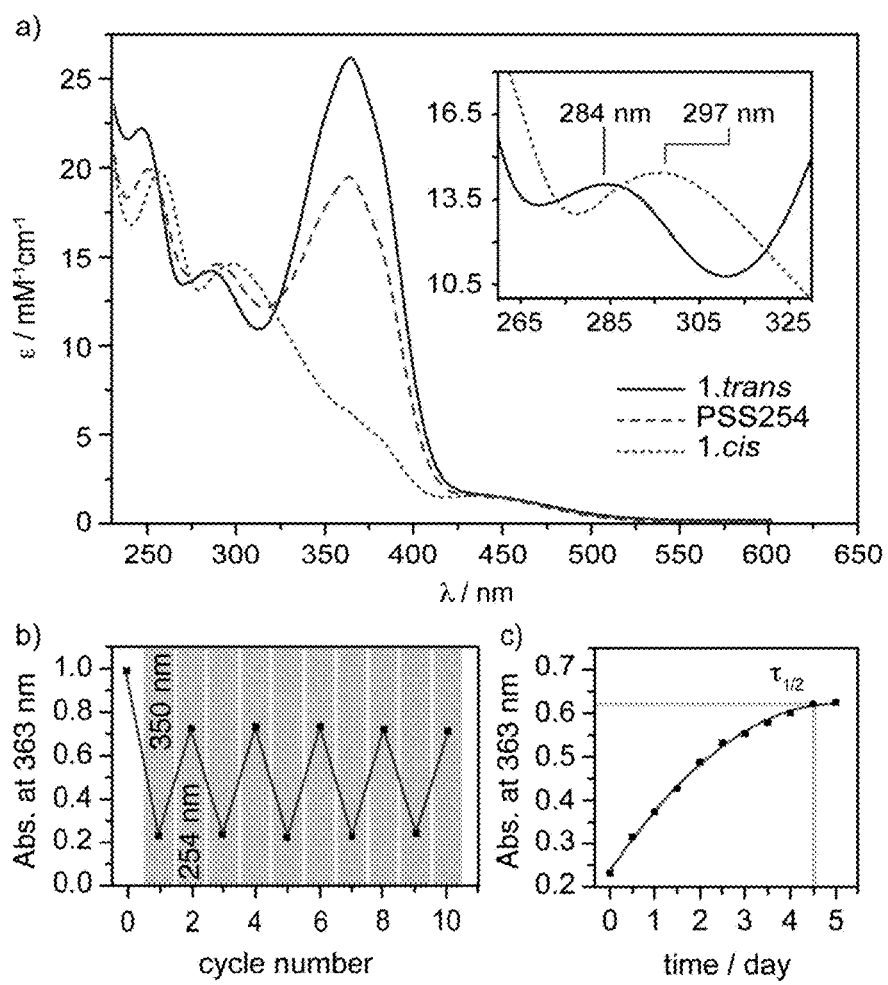
FIG. 2 shows in (a) an absorption spectrum of 1.trans (solid), 1.cis (dotted), and the photostationary state PSS254 (dashed) in tetrahydrofuran (THF) solution; the inset shows the S0→S1 band of the phenylene-bithiophene segment on an enlarged scale, in (b) measured absorbance at λ=363 nm of 1 in THF solution alternating irradiation at λ=350 and λ=254 nm in repeated switching cycles, and in (c) measured absorbance at λ=363 nm of 1.cis in THF solution during the thermal relaxation.

The absorption spectra of the 1.trans and 1.cis are the superposition of individual constituting components, namely the azobenzene, in its trans and cis form, and the phenylene-bithiophene segment. The absorption spectrum of 1.trans displays four distinguishable peaks: 454 nm, 363 nm, 284 nm and 245 nm (see FIG. 2a). The first two bands correspond to the typical $S_0 \rightarrow S_1$ and $S_0 \rightarrow S_2$ excitations represented respectively by the n–π* and π–π* transitions localized on the azobenzene. The peak centered at 284 nm is mainly the result of the $S_0 \rightarrow S_1$ excitation of the phenyl-functionalized bithiophene. In the framework of the molecular orbitals, this excitation can be describe as a HOMO→LUMO single particle transition involving the π and π* orbitals prevalently localized on the bithiophene. The last band at 245 nm, is the results of a high-energy electronic transition involving the it π–π* orbitals localized on phenyl rings of the azobenzene. Upon irradiation at 350 nm around 86% of the trans isomer of azobenzene is converted to the cis form (see FIG. 2a).

The resulting absorption spectrum, 1.cis, exhibits the typical signature of the azobenzene in its cis conformation, with a reduction of the oscillation strength for the it π–π* transition (absorption intensity at 363 nm ~23%). However, no significant changes in the absorption profile were observed for the S0→S1 (n–π*) transition. Conversely, bands at 284 nm and 245 nm exhibit a bathochromic shift of 13 nm and 11 nm, respectively (see FIG. 2a).

Since the π-conjugation extension of the bithiophene is directly correlated with the peak at 284 nm, any conformational change in its π-bonds geometry will result in a spectral shift of this band. According to the spectral changes, the red-shift observed for this band is ascribable to a planarization of bithiophenic segment leading to a more efficient delocalization of its molecular orbitals along the two thiophene units. After the trans-to-cis isomerization of 1, it is possible to recover about ~55% of the initial trans isomer by irradiating at 254 nm (photostationary state (PSS), see FIG. 2a).

The later wavelength was selected as an alternative excitation to the usual 430 nm due to the similar oscillator strengths of the n–π* band for the two conformers. Monitoring the UV-Vis absorptions of 1 after many repeated alternating irradiation cycles at λ=350 nm and at λ=254 nm, respectively, did not result in any noticeable degradation of the compound, highlighting the robustness of the PTS architecture (see FIG. 2b). The recovery of the initial 1.trans conformer can also be obtained by thermal relaxation of the azobenzene moiety with a half-life ($\tau_{1/2}$) of ca. 4.5 days at 25° C. (see FIG. 2c). Such long thermal stability is not common for unsubstituted alkoxy-azobenzene derivatives. Slow thermal relaxation is usually observed in azobenzenes that are functionalized in the ortho position with electron donating and withdrawing groups. The lack of electron directing functionality in the PTS azobenzene, and the faster thermal relaxation of its open precursor and pristine azobenzene suggest that the slow thermal relaxation of 1.cis can be associated to a reduced degree freedom in the isomerization motion.

Figure 3:
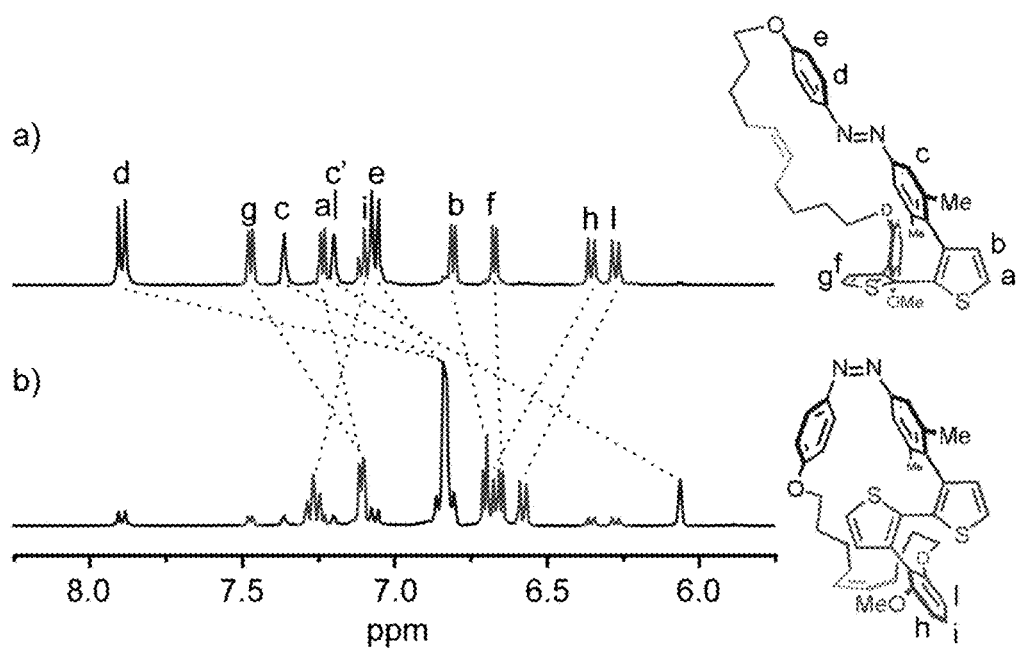
FIG. 3 shows the aromatic region of the $^1$H-NMR spectrum of compound 1 in tetrahydrofuran-d8; before (a) and after 1 h of irradiation at 350 nm (b).

Finally, $^{1}$H-NMR spectroscopy was conducted to investigate the rotation along the thiophene-thiophene bond on the isomerization of the azobenzene moiety. After the trans-to-cis isomerization of 1, the aromatic protons of thiophene $H_g$ (δ 7.47 ppm) and $H_h$ (δ 6.81 ppm) showed significant up-field shifts by 0.36 and 0.11 ppm, respectively (FIG. 3). On the other hand, aromatic signals of the phenylene of the linker, $H_i$, $H_l$ and $H_h$, observed respectively at 7.10, 6.36, and 6.28 ppm for 1.trans, showed downfield shifts by 0.17, 0.33, and 0.30 ppm, respectively. These spectral changes are reasonable given the different molecular geometry assumed by the two PTS conformers. In 1.trans, thiophene units assume a synclinal arrangement, orienting two phenyl fragments of the linker and azobenzene in a parallel-displaced conformation. Such arrangement leads to the lowering of the magnetic shielding effect in the thiophenes (downfield shift) while increasing that of the phenylenes due to π–π stack interactions (upfield shift). On the other end, when the azobenzene isomerizes to its cis form, the thiophenes assume a more planar conformation with concomitant edge-to-face arrangement with corresponding pseudo-orthogonal phenyl rings of the linker and azobenzene.

This conformation results in an increase in the magnetic shielding of the thiophene protons (upfield shift), and a decrease in the shielding of the phenylene counterpart (downfield shift). The resulting $^{1}$H-NMR spectral profile of 1.cis is in good agreement with bithiophene signature of the open analogue and with 'planarly constrained' bithiophenes as previously reported. Hence, it can be concluded that compound 1 undergoes a rotation-like (twisted-planar) motion along the thiophene-thiophene bond upon trans-cis isomerization of the azobenzene switch. In conclusion, a novel molecular actuator has been designed capable of modulating the extension of its π-conjugated backbone in response to light. The mechanical motion associated with the trans-cis isomerization of an azobenzene has been translated to a change in the planarity of the connected bithiophene, thus allowing for the dynamic tuning of its π-conjugation. This provides a basis for the novel molecular actuators that can be used to tune the physical properties of extended π-conjugated system. The the proposed PTS structure can be integrated into π-conjugated oligomers and polymers, i.e. via the terminal α-thiophene positions, can potentially lead to the next-generation of photochromic molecular materials with both photochromic and photoconductive behavior, and allow for the fabrication of novel light responsive optoelectronic devices.

The invention claimed is:
1. A compound having the following formula:

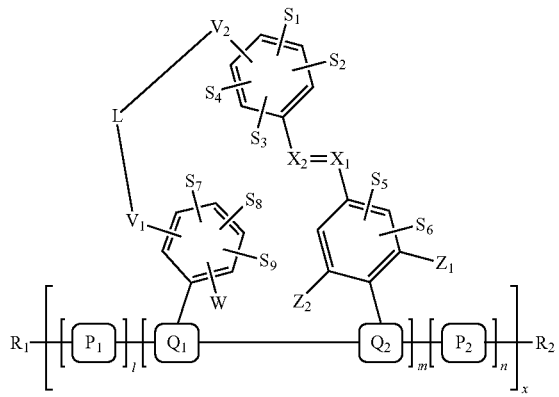

wherein
$Q_1$, $Q_2$ are one or a mixture of π-conjugated aromatic cores;
$R_1$ and $R_2$ are selected, independently from each other, from the following group: H, halogen, methyl, Sn $(R_{R,1})_3$, $B(OH)_2$, $OR_{R,2}$, $NR_{R,3}R_{R,4}$, $NO_2$, $COOR_{R,5}$, $COR_{R,6}$, $SR_{R,7}$, —CN, —CCR_{R,8}, —SO$_3$H, —CH=C(CN)$_2$, —CH=C(CN)(COOR_{R,9}), —C(CN)=C(CN)$_2$, substituted and unsubstituted ferrocene and derivatives thereof, substituted and unsubstituted pyridine and derivatives thereof, pentafluorophenol, and substituted and unsubstituted fullerene and derivatives thereof; with the residues $R_{R,1}$-$R_{R,9}$ selected, independently from each other, from the group consisting of: methyl, ethyl, propyl, isopropyl, phenyl, benzyl, and primary, secondary, and tertiary amines;
$V_1$ and $V_2$ are selected, independently from each other, from the following group: $CH_2$, S, O, NH, COO, CO, $CONR_{V,1}$, and $NR_{V,2}CO$, with the residues $R_{V,1}$ and $R_{V,2}$ selected, independently from each other, from the group consisting of H, methyl, ethyl, propyl, isopropyl, phenyl and benzyl;
$X_1$ and $X_2$ are selected, independently from each other, from the following group: N, and CH;
$Z_1$ and $Z_2$ are selected, independently from each other, from the following group: halogen, methyl, ethyl, propyl, isopropyl, phenyl, benzyl, $SR_{Z,1}$, $OR_{Z,2}$, $COOR_{Z,3}$, $NR_{Z,4}R_{Z,5}$ $NO_2$, —CN, and —SO$_3$H, with the residues $R_{Z,1}$-$R_{Z,5}$ selected, independently from each other, from the group consisting of H, methyl, ethyl, propyl, isopropyl, benzyl, primary amines, secondary amines, and tertiary amines;
L is a hydrocarbon chain with 5-15 carbon atoms in which up to 3 hydrocarbon moieties (—CH$_2$—) can be replaced by one of the following moieties: O, $NR_{L,1}$, S, and/or in which there can be up to 3 double or triple bonds, in which pairs of the type —CH$_2$—CH$_2$— are replaced by —C≡C—, —$R_{L,2}$C=$CR_{L,3}$-, or —N=$CR_{L,4}$-, with the residues $R_{L,1}$-$R_{L,4}$ selected, independently from each other, from the group consisting of H, methyl, ethyl, propyl, isopropyl and benzyl;
W is selected from the group consisting of: H, halogen, $SR_{W,1}$, methyl, ethyl, $OR_{W,2}$, and $COOR_{W,3}$, with the residues $R_{W,1}$-$R_{W,3}$ selected, independently from each other, from the group consisting of H, methyl, ethyl, propyl, isopropyl, phenyl and benzyl;

$S_1$—$S_9$ are selected, independently from each other, from the group consisting of: H, halogen, methyl, ethyl, phenyl, benzyl, $OR_{S,1}$, $SR_{S,2}$, $COOR_{S,3}$, $C(=O)R_{S,4}$, $NR_{S,5}R_{S,6}$, $NO_2$, and $SO_3H$, with the proviso that pairs of $S_1$-$S_4$, $S_5$ and $S_6$, pairs of $S_7$-$S_9$ can be given by bridging conjugated structural elements selected from the group consisting of:

ortho $(CH)_2$-benzene,

—$(CR_{S,9})(CR_{S,10})(CR_{S,11})$—, —$(CR_{S,12})(CR_{S,13})(CR_{S,14})(CR_{S,15})$—, and —$(CR_{S,16})(CR_{S,17})(CR_{S,18})(CR_{S,19})(CR_{S,20})$—, in which $CR_{S,N}$ moieties can be replaced by N, NH, O, and/or S, with the residues $R_{S,1}$-$R_{S,20}$ selected from the group consisting of H, methyl, ethyl, propyl, isopropyl, phenyls and benzyl $P_1$, $P_2$ are one or a mixture of π-conjugated aromatic cores l is selected to be an integer in the range of 0-10 m is selected to be an integer in the range of 1-10 n is selected to be an integer in the range of 0-10 x is selected to be an integer in the range of 1-10,000 with the proviso that l+n is at least 1.

2. The compound according to claim 1, wherein at least one of $P_1$ and $P_2$ is selected from the group consisting of at least one of: 2,1,3-benzothiadiazole, azole, diazole, triazole, tetrazole, thiophene, pyrrole, furane, selenophene, vinylene, selenazole, thiazole, thiadiazole, oxazole, oxadiazole, pyridine, diazine, triazine, tetrazine, selenazine, thiazine, azepine, diazepine, phenyl based cores, biphenyl based cores, arylamine derivatives, tetraphenylbenzidine, carbazole, pyrrole-based macrocycles, boron derivatives, difluoroboradiaza indacene, ethylenedioxythiophene, phosphorus derivatives, perylene derivatives, N,N dialkyl perylene dicarboximide, N,N dibenzyl perylene dicarboximide, naphthalene derivatives, N,N dialkyl naphthalene dicarboximide, N,N dibenzyl naphthalene dicarboximide, polycyclic aromatic hydrocarbons, thienothiophene and its derivatives, benzodithiophene and its derivatives, and tetrathiafulvalene and its derivatives.

3. The compound according to claim 1, wherein at least one of $P_1$ and $P_2$ is selected to be thiophene or a bridged π-conjugated biphenyl.

4. The compound according to claim 1, wherein one of $Q_1$ and $Q_2$ is given by one of the following structural moieties:

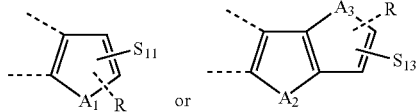

wherein R is $R_1$ or $R_2$, respectively, $A_1$, $A_2$, and $A_3$ are selected, independently from each other, from the following group: S, O, NH, $NR_{A,1}$, BH, $BR_{A,1}$, $PR_{A,1}$, $PR_{A,1}R_{A,2}$, Se, CH=CH, CH=N, CH=$PR_{A,1}$, CH=$PR_{A,1}R_{A,2}$, $CH_2$, C=O, C=$CH_2$, and C=$CR_{A,1}R_{A,2}$, with the residues $R_{A,1}$ and $R_{A,2}$ selected, independently from each other, from the group consisting of H, methyl, ethyl, propyl and benzyl;

$S_{11}$ and $S_{13}$ are selected, independently from each other, from the group consisting of: H, halogen, methyl, ethyl, phenyl, benzyl, $OR_{S,21}$, $SR_{S,22}$, $COOR_{S,23}$, $C(=O)R_{S,24}$, $NR_{S,25}R_{S,26}$, $NO_2$, and $SO_3H$, with the residues $R_{S,21}$-$R_{S,26}$ selected from the group consisting of H, methyl, ethyl, propyl, isopropyl, phenyl and benzyl.

5. The compound according to claim 4, wherein S11 and S13 are each selected to be H.

6. The compound according to claim 1, wherein $Q_1$-$Q_2$ are each selected to be thiophene.

7. The compound according to claim 1, wherein $X_1$ and $X_2$ are each selected to be N.

8. The compound according to claim 1, wherein $V_1$ and $V_2$ are each selected to be O.

9. The compound according to claim 1, wherein $Z_1$ and $Z_2$ are each selected to be methyl.

10. The compound according to claim 1, wherein W is selected from the group consisting of methyl and methoxy.

11. The compound according to claim 1, wherein L is selected to be a hydrocarbon chain with 8-12 carbon atoms, in which up to 2 hydrocarbon moieties can be replaced by one of the following moieties: O, NH, S, and in which there can be up to 2 carbon-carbon double or triple bonds.

12. The compound according to claim 1, wherein L is selected to be a $(CH_2)$ chain with 8-12 carbon atoms, and two of the $(CH_2)$ moieties are replaced by (CH) to form a double bond.

13. The compound according to claim 1, wherein L is selected to be a $(CH_2)$ chain with 10 carbon atoms, and two of the $(CH_2)$ moieties are replaced by (CH) to form a double bond at the position of the fifth carbon atom of the chain of L.

14. The compound according to claim 1, wherein $S_1$-$S_9$ are each selected to be H.

15. The compound according to claim 1, wherein x is selected to be an integer in the range of 10-1000.

16. The compound according to claim 1, wherein at least one of P1 and P2 is selected from the group consisting of at least one of: 2,1,3-benzothiadiazole, azole, imidazole and pyrazole, triazole, tetrazole, thiophene, pyrrole, furane, selenophene, vinylene, selenazole, thiazole, thiadiazole, oxazole, oxadiazole, pyridine, pyrimidine, triazine, tetrazine, selenazine, thiazine, azepine, diazepine, phenyl based cores, biphenyl based cores, triphenylamine, tetraphenylbenzidine, carbazole, porphyrin, phthalocyanine, triphenylborane, difluoroboradiaza indacene, ethylenedioxythiophene, triphenylphosphine, triphenylphosphine oxide, perylene tetracarboxylic dianhydride, N,N dialkyl perylene dicarboximide, N,N dibenzyl perylene dicarboximide, naphthalene tetracarboxylic dianhydride, N,N dialkyl naphthalene dicarboximide, N,N dibenzyl naphthalene dicarboximide, anthracene, tetracene, pentacene, pyrene, thienothiophene and its derivatives, benzodithiophene and its derivatives, and tetrathiafulvalene and its derivatives.

17. An optical, electronic or electro-optics device comprising a compound according to claim 1.

18. The device according to claim 17, wherein the device is a photochromic photovoltaic device, a multicolour organic light emitting diodes device, or a photo tuneable organic field effect transistor.

19. An optical, electronic or electro-optics device comprising a compound according to claim 1, wherein the device comprises a substrate and at least one layer on said substrate, said layer including at least one said compound.

20. A method for making an optical, electronic or electro-optics device comprising:

making at least one layer including at least one compound according to claim 1 on a substrate.

* * * * *